United States Patent [19]

Cosmo et al.

[11] Patent Number: 5,539,114

[45] Date of Patent: Jul. 23, 1996

[54] PROCESS FOR THE PREPARATION OF SUBSTITUTED QUINAZOLINE-2,4,-DIONES

[75] Inventors: Robert Cosmo, Darmstadt; Wolfgang Tronich, Eppstein, both of Germany

[73] Assignee: Hoechst AG, Germany

[21] Appl. No.: 339,948

[22] Filed: Nov. 15, 1994

[30] Foreign Application Priority Data

Nov. 17, 1993 [DE] Germany .................. 43 39 209.1

[51] Int. Cl.⁶ .......................................... C07D 239/96
[52] U.S. Cl. ................................................ 544/285
[58] Field of Search .............................. 544/285

[56] References Cited

U.S. PATENT DOCUMENTS

| | | | |
|---|---|---|---|
| 4,058,612 | 11/1977 | Neustadt | 424/251 |
| 4,059,627 | 11/1977 | Kritzler et al. | 260/580 |
| 4,405,623 | 9/1983 | Ishikawa et al. | 544/116 |
| 4,506,089 | 3/1985 | Hackenberger et al. | 560/70 |
| 5,201,362 | 4/1993 | Yamagami et al. | 164/480 |

FOREIGN PATENT DOCUMENTS

| | | |
|---|---|---|
| 0040793 | 12/1981 | European Pat. Off. |
| 0360417 | 3/1990 | European Pat. Off. |
| 0546206 | 6/1993 | European Pat. Off. |
| 1804391 | 5/1970 | Germany . |
| 2345788 | 5/1974 | Germany . |
| 3712782 | 11/1988 | Germany . |
| 4334432 | 4/1995 | Germany . |
| 50-14689 | 2/1975 | Japan . |
| 1059271 | 2/1967 | United Kingdom . |

OTHER PUBLICATIONS

Ogawa et al., Chemical and Pharmaceutical Bulletin, 1988, 36(6), 2253–2258.
Schneller et al., Journal of Medicinal Chemistry, 1989, 32(10), 2247–2254.
Schneller et al., Journal of Medicinal Chemistry, 1986, 29(6), 972–978.
Venuti et al., Journal of Medicinal Chemistry, 1988, 31(11), 2136–2145.
Ishikawa et al., Chemical and Pharmaceutical Bulletin, 1985, 33(8), 336–3348.
Hammen et al., Journal of Heterocyclic Chemistry, 1987, 24(6), 1701–1703.
Chemical Abstracts, vol. 83, No. 11, Abstract No. 97348u, p. 596, Sep. 15, 1975.
Lespagnol, A., et al, *Eur. J. Med. Chem.* 9:263–268 (1974).
Papadopoulos, E. P., et al, *J. Heterocyclic Chem.* 19:269–272 (1982).

*Primary Examiner*—Mukund J. Shah
*Assistant Examiner*—Matthew V. Grumbling
*Attorney, Agent, or Firm*—Connolly & Hutz

[57] ABSTRACT

A process for the preparation of quinazoline-2,4-diones of the formula (I)

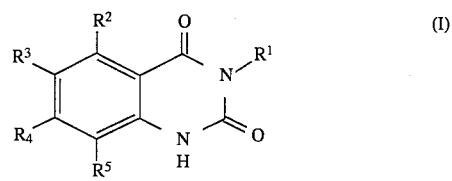

in which $R^1$ is aryl and $R_2$, $R^3$, $R^4$, and $R^5$ independently of one another are halogen, alkyl, alkoxy or hydrogen, by reacting anthranilic acid esters of the formula (II)

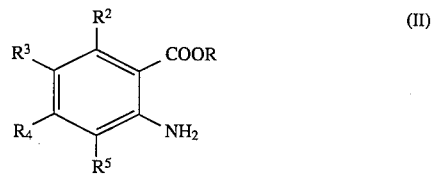

in an aprotic reaction medium with aryl isocyanates $R^1$—N=C=O to give N-arylcarbamoyl-anthranilic acid esters of the formula (III)

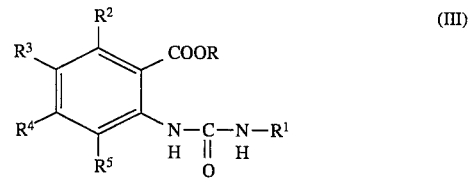

and cyclizing these in the presence of a base selected from the group of alkali metal or alkaline earth metal alkoxides, amides, hydrides or tetraalkylammonium hydroxides.

14 Claims, No Drawings

PROCESS FOR THE PREPARATION OF SUBSTITUTED QUINAZOLINE-2,4,-DIONES

Substituted quinazoline-2,4-diones of the formula (I) are interesting intermediates for pharmaceuticals and plant protection agents (U.S. Pat. No. 4,405,623; GB 1,059,271; EP 360,417).

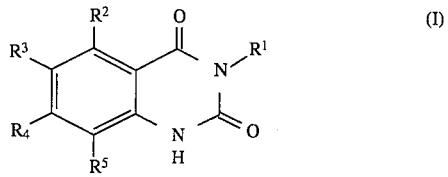

(I) are customarily prepared in two reaction steps:

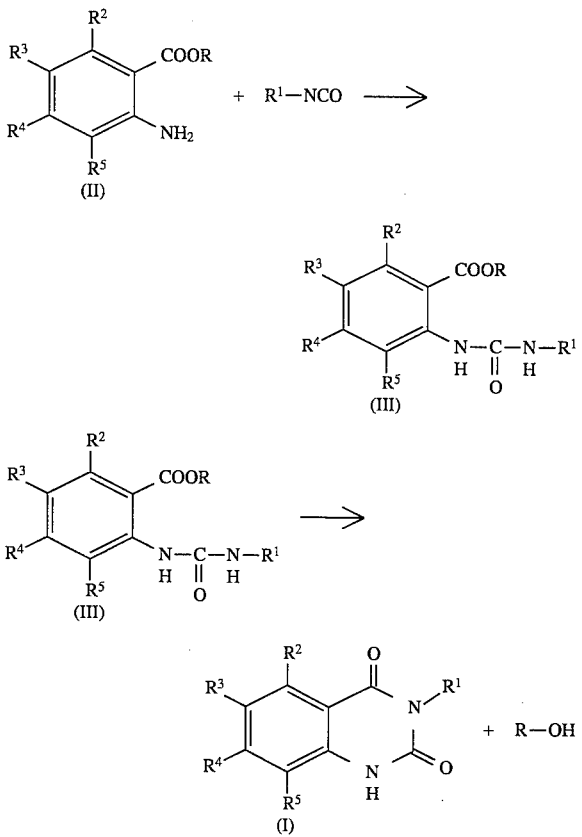

In the first stage, the intermediate (III) is obtained by reaction of an anthranilic acid or of an alkyl anthranilate, which may be substituted, of the formula (II) with an aryl isocyanate in a reaction medium which is inert to isocyanates.

In the case of anthranilic acids, N-arylcarbamoylanthranilic acids (III, R=H) are thus obtained, which are intermediately isolated, optionally purified by recrystallization and then ring-closed in a second reaction step, e.g. in polyphosphoric acid, in the course of 5 hours at 150° C. (EP 360,417 A1) or a protic, organic medium, such as e.g. ethanol, in the presence of excess strong mineral acid, preferably gaseous hydrochloric acid, to give quinazoline-2,4-diones of the formula (I) (GB 1,059,271, Example 3).

In a corresponding manner, on reaction with aryl isocyanates the alkyl anthranilates yield alkyl N-arylcarbamoylanthranilates (III, R=alkyl) which are intermediately isolated and can be cyclized to the quinazolinediones in an analogous manner to the acids. For compounds (III), R=alkyl, it is also known to carry out the cyclization to (I) in protic media such as e.g. ethanol or methanol in the presence of aqueous sodium hydroxide [German Offenlegungsschrift 1,804,391 (Example 4); J. Heterocycl. Chem., 19 (2) p. 269 (1982)].

These preparation processes for substituted quinazoline-2,4-diones, however, have the significant disadvantage that the preparation of the intermediates (III) is always carried out in another reaction medium than the cyclization of (III) to (I).

This fact is obviously based on the preconception that the ring closure of (III) to (I) can only be carried out in protic, strongly polar media, such as e.g. in alcohols, strong mineral acids or alcoholic/aqueous alkaline media. As has been proven, however, these media for their part are unsuitable for the preparation of (III) from (II) and aryl isocyanates, as they react extremely vigorously with isocyanates themselves. This fact thus leads to the use of a different reaction medium for the preparation of (III) and (I) and thus inevitably to increased technical and economic expenditure, which is naturally associated with a change of the reaction medium and an intermediate product isolation.

In Europ. J. Med. Chem., 9, p. 263 (1974), it was described that the reaction of methyl anthranilate (II, $R=CH_3$, $R^2$, $R^3$, $R^4$, $R^5=H$) with aryl isocyanates to give the methyl N-arylcarbamoylanthranilate (III, $R=CH_3$) and the subsequent cyclization to quinazoline-2,4-diones (I) can be carried out in the same reaction medium (benzene or toluene).

Sub-stoichiometric amounts of triethylamine are employed as a cyclization catalyst here. The reaction can also proceed without solvent. This process, however, has the disadvantage that high reaction temperatures or long reaction times are necessary in order to convert the intermediate alkyl N-arylcarbamoylanthranilates (III, R=alkyl) to the quinazoline-2,4-dione (I). In general, the products of this process are contaminated with the intermediate alkyl N-arylcarbamoylanthranilate (III, R=alkyl). In general, a complete cyclization can only be achieved by use of excess triethylamine.

In spite of very short reaction times and good yields, the already-mentioned cyclization of (III) where R=alkyl to give (I) in methanol or ethanol as a reaction medium and using a super-stoichiometric amount of about 5 to 10% strength aqueous sodium hydroxide [German Offenlegungsschrift 1,804,391 (Example 4, P. 15); J. Heterocycl. Chem. 19 (2) P. 269 (1982)] has the disadvantage that the sodium salt of quinazoline-2,4-dione is first obtained here, which then has to be converted into the free dione by treatment with a mineral acid or an organic acid, 1 mol of undesired, waste water-polluting sodium salt of the mineral acid or of the organic acid resulting.

There was thus a great need for a process which enables substituted quinazoline-2,4-diones to be obtained in high yield and purity in a technically simple manner with low environmental pollution.

This object has been achieved by a process for the preparation of quinazoline-2,4-diones of the formula (I)

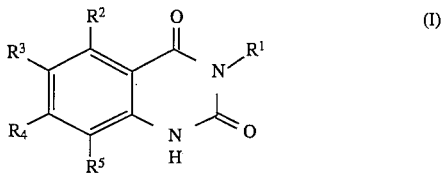

in which $R^1$ is aryl and $R^2$, $R^3$, $R^4$ and $R^5$ independently of one another are halogen, alkyl, alkoxy or hydrogen, which comprises reacting anthranilic acid esters of the formula (II)

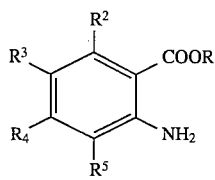
(II)

in which R is alkyl and $R^2$ to $R^5$ have the meaning indicated above, in an aprotic reaction medium with aryl isocyanates $R^1$—N=C=O to give N-arylcarbamoylanthranilic acid esters of the formula (III)

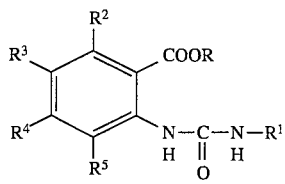
(III)

in which R and $R^1$ to $R^5$ have the meaning indicated above, and cyclizing these in the presence of alkali metal or alkaline earth metal alkoxides, amides, hydrides or tetraalkylammonium hydroxides. Of particular interest is the process for the preparation of compounds of the formula I in which $R^1$ is phenyl which can be substituted by halogen, $(C_1-C_4)$-alkyl or $(C_1-C_4)$-alkoxy, R is $(C_1-C_3)$-alkyl and $R^2$ to $R^5$ independently of one another are hydrogen, $(C_1-C_3)$-alkyl, $(C_1-C_3)$-alkoxy, fluorine, chlorine or bromine. In this connection, in turn, the compounds are important in which $R^2$ to $R^5$ independently of one another are hydrogen, fluorine, chlorine or methyl.

The cyclization of (III) to (I) proceeds in outstanding yields in aprotic reaction media which, as such, are inert to isocyanates. Preferably, the same reaction media are used in which the compound (III) is also prepared, such as e.g. aromatic, aliphatic or cycloaliphatic hydrocarbons, heterocycles or ketones, in particular mononuclear alkylaromatics or, under normal conditions, liquid alkanes and cycloalkanes. In many cases, toluene and xylenes in pure form or as an isomer mixture have proven suitable.

The advantageous possibility thus exists of carrying out the reaction of (II) with the aryl isocyanate to give (III) and the cyclization of (III) to (I) in one and the same reaction medium at low temperatures with very short reaction times; in this case an intermediate isolation of (III) can be dispensed with. However, it is also possible to isolate (III), e.g. for reasons of additional purification, and then to cyclize to (I) again in fresh reaction medium.

In general, the anthranilic acid esters employed are the alkyl esters; substituted methyl anthranilates, in particular fluoro-substituted methyl anthranilates, whose preparation is described, for example, in German Patent Application P 43 34 432.1 are preferably used.

The alkali metal or alkaline earth metal alkoxides used as a base can be employed in substance or as solutions in the corresponding alcohols. In many cases, the use of sodium methoxide in methanol has proven suitable.

If alkali metal or alkaline earth metal hydrides or amides are used, these can likewise be employed in substance or as a suspension in the aprotic solvent.

The bases used are customarily employed in amounts from 1 to 95 mol % based on the N-arylcarbamoylanthranilic acid esters (III). It has proven convenient to use amounts of from 1 to 20 mol %, in particular from 5 to 10 mol %.

Compared with the preparation route described in Europ. J. Med. Chem., 9, p. 263 (1974), the process for the preparation of quinazoline-2,4-diones according to the invention has the following significant advantages: when using the bases according to the invention, distinctly shorter reaction times and lower temperatures are necessary for the complete cyclization of the alkyl N-arylcarbamoylanthranilates (III) to the quinazoline- 2,4-dione (I) than when using triethylamine (see Examples 1 and 5.1, and also Examples 6.1 and 6.2). The quinazoline-2,4-diones of the formula (I) are additionally obtained in better yield and in better purity.

In general, the reaction temperature for the reaction of the methyl anthranilate with the aryl isocyanate is between about 20° C. and the boiling point of the reaction medium used, preferably in a range between 30° and 120° C. The reaction temperature of the cyclization of (III) to (I) is expediently chosen such that the alcohol liberated distils off from the reaction medium; in the case of the preferred methyl or ethyl ester of (II) this corresponds to a reaction temperature above the boiling point of methanol or ethanol respectively.

EXAMPLES

Example 1

Preparation of 3-(4-chlorophenyl)- 2,4-(1H,3H)-quinazolinedione

A solution of p-chlorophenyl isocyanate (15.3 g, 0.10 mol) in toluene (50 ml) is metered at room temperature into a solution of methyl anthranilate (15.1 g, 0.10 mol) in toluene (100 ml). After addition is complete, the mixture is stirred at 90° C. for 2 hours. 1.80 ml of a 30% strength solution of methanolic sodium methoxide (0.010 mol) are metered in and the mixture is stirred at 90° C. for a further 1 hour, methanol being distilled off. After cooling, the product is filtered off with suction and washed with 3×20 ml of toluene. The toluene-moist precipitate is treated with dilute sulfuric acid and the residual toluene is removed by azeotropic distillation. The product is then filtered off with suction, washed with water and dried. 26.8 g of 3-(4-chlorophenyl)- 2,4(1H,3H)-quinazolinedione (yield: 98.3% of theory) of melting point 290° to 292° C. are obtained.

Example 2

Preparation of 3-(4-tolyl)- 2,4(1H, 3H) -quinazolinedione

A solution of p-tolyl isocyanate (133.2 g, 1.00 mol) in xylene (300 ml) is metered at room temperature into a solution of ethyl anthranilate (165.2 g, 1.00 mol) in xylene (600 ml). After addition is complete, the mixture is stirred at 90° C. for 2.5 hours. 18.0 ml of a 30% strength solution of methanolic sodium methoxide (0.10 mol) are metered in and the mixture is stirred at 90° C. for a further 2 hours, ethanol and methanol being distilled off. After cooling, the product is filtered off with suction and washed with 3×75 ml of xylene. The xylene-moist precipitate is treated with dilute hydrochloric acid and the residual xylene is removed by azeotropic distillation. The product is then filtered off with suction, washed with water and dried. 233.0 g of 3-(4-tolyl)-2,4(1H,3H)-quinazolinedione (yield 92.4% of theory) of melting point 267° C. (lit 265° to 266° C.) are obtained.

Example 3

Preparation of 6-fluoro-3-(3-tolyl)-2,4(1H,3H)-quinazolinedione

A solution of m-tolyl isocyanate (33.3 g, 0.25 mol) in xylene (100 ml) is metered at room temperature into a solution of ethyl 4-fluoroanthranilate (45.8 g, 0.25 mol) in xylene (250 ml). After addition is complete, the mixture is stirred at 90° C. for 2.5 hours. 32.5 ml of a 20% strength solution of aqueous tetrabutylammonium hydroxide (0.025 mol) are metered in and the mixture is stirred at 90° C. for a further 2 hours, ethanol being distilled off. After cooling, the product is filtered off with suction and washed with 3×30 ml of xylene. The xylene-moist precipitate is treated with dilute hydrochloric acid and the residual xylene is removed by azeotropic distillation. The product is then filtered off with suction, washed with water and dried. 62.0 g of 6-fluoro-3-(3-tolyl)-2,4(1H,3H)-quinazolinedione (yield: 91.7% of theory) of melting point 278° to 279° C. are obtained.

Example 4

Preparation of 3-(2-tolyl)-6,7-dimethoxy-2,4(1H,3H)-quinazolinedione

A solution of o-tolyl isocyanate (13.3 g, 0.10 mol) in toluene (40 ml) is metered at room temperature into a solution of methyl 4,5-dimethoxyanthranilate (21.1 g, 0.10 mol) in toluene (70 ml). After addition is complete, the mixture is stirred at 90° C. for 2 hours. 1.80 ml of a 30% strength solution of methanolic sodium methoxide (0.010 mol) are metered in and the mixture is stirred at 90° C. for a further 1 hour, methanol being distilled off. After cooling, the product is filtered off with suction and washed with 3×30 ml of toluene. The toluene-moist precipitate is treated with dilute sulfuric acid and the residual toluene is removed by azeotropic distillation. The product is then filtered off with suction, washed with water and dried. 29.0 g of 3-(2-tolyl)-6,7-dimethoxy- 2,4(1H,3H)-quinazolinedione (yield: 92.9% of theory) of melting point 282° to 284° C. are obtained.

Examples 5.1–5.4

Preparation of 3-(2,4-dichlorophenyl)-6-fluoro-2,4(1H,3H)-quinazolinedione in Various Solvents

Example 5.1

Preparation of 3-(2,4-dichlorophenyl)-6-fluoro-2,4(1H,3H)-quinazolinedione in Xylene A solution of 2,4-dichlorophenyl isocyanate (47.0 g, 0.25 mol) in xylene (130 ml) is metered at room temperature into a solution of ethyl 5-fluoroanthranilate (45.2 g, 0.25 mol) in xylene (210 ml). After addition is complete, the mixture is stirred at 90° C. for 2.5 hours. 4.50 ml of a 30% strength solution of methanolic sodium methoxide (0.025 mol) are metered in and the mixture is stirred at 90° C. for a further 2 hours, ethanol and methanol being distilled off. After cooling, the product is filtered off with suction and washed with 3×30 ml of xylene. The xylene-moist precipitate is treated with dilute hydrochloric acid and the residual xylene is removed by azeotropic distillation. The product is then filtered off with suction, washed with water and dried. 73.4 g of 3-(2,4 dichlorophenyl)-6-fluoro- 2,4(1H,3H)-quinazolinedione (yield: 90.3% of theory) of melting point 313° to 314° C. are obtained.

Example 5.2

Preparation of 3-(2,4-dichlorophenyl)-6-fluoro-2,4(1H,3H)-quinazolinedione in Acetone A solution of 2,4-dichlorophenyl isocyanate (18.8 g, 0.10 mol) in acetone (50 ml) is metered at room temperature into a solution of ethyl 5-fluoroanthranilate (18.3 g, 0.10 mol) in acetone (70 ml). After addition is complete the mixture is stirred at 90° C. for 2.5 hours. 1.80 ml of a 30% strength solution of methanolic sodium methoxide (0.010 mol) are metered in and the mixture is stirred under reflux for a further 2 hours. After cooling, the product is filtered off with suction and washed with 3×15 ml of acetone. The acetone-moist precipitate is treated with dilute hydrochloric acid and the residual acetone is removed by azeotropic distillation. The product is then filtered off with suction, washed with water and dried. 31.7 g of 3-(2,4-dichlorophenyl)-6-fluoro-2,4(1H,3H)-quinazolinedione (yield: 97.5% of theory) of melting point 313° to 314° C. are obtained.

Example 5.3

Preparation of 3-(2,4-dichlorophenyl)-6-fluoro-2,4(1H,3H)-quinazolinedione in Hexane 2,4-dichlorophenyl isocyanate (18.8 g, 0.10 mol) is introduced in portions at room temperature into a solution of ethyl 5-fluoroanthranilate (18.3 g, 0.10 mol) in hexane (120 ml). After addition is complete, the mixture is stirred under reflux for 2 hours. 3.60 ml of a 30% strength solution of methanolic sodium methoxide (0.020 mol) are metered in and the mixture is stirred under reflux for a further 2 hours, ethanol and methanol being distilled off. After cooling, the product is filtered off with suction and washed with 3×15 ml of hexane. The hexane-moist precipitate is treated with dilute hydrochloric acid and the residual hexane is removed by azeotropic distillation. The product is then filtered off with suction, washed with water and dried. 31.2 g of 3-(2,4-dichlorophenyl)-6-fluoro-2,4(1H,3H) -quinazolinedione (yield: 96.0% of theory) of melting point 312° to 314° C. are obtained.

Example 5.4

Preparation of 3-(2,4-dichlorophenyl)-6-fluoro-2,4(1H,3H)-quinazolinedione in N-methylpyrrolidone A solution of 2,4-dichlorophenyl isocyanate (18.8 g, 0.10 mol) in N-methylpyrrolidone (50 ml) is metered at room temperature into a solution of ethyl 5-fluoroanthranilate (18.3 g, 0.10 mol) in N-methylpyrrolidone (70 ml). After addition is complete, the mixture is stirred at 90° C. for 2 hours. 1.80 ml of a 30% strength solution of methanolic sodium methoxide (0.010 mol) are metered in and the mixture is stirred under reflux for a further 2 hours, ethanol and methanol being distilled off. After cooling, the product is precipitated by addition of dilute hydrochloric acid (100 ml). The product is then filtered off with suction, washed with water and dried. 29.8 g of 3-(2,4-dichlorophenyl)-6-fluoro-2,4(1H,3H)-quinazolinedione (yield: 91.7% of theory) of melting point 311° to 313° C. are obtained.

Example 6.1

Preparation of 3-(4-chlorophenyl)-2,4(1H,3H)-quinazolinedione in Toluene (Catalyst: Triethylamine)—Analogously to Example 1

A solution of p-chlorophenyl isocyanate (15.3 g, 0.10 mol) in toluene (50 ml) is metered at room temperature into a solution of methyl anthranilate (15.1 g, 0.10 mol) in toluene (100 ml). After addition is complete, the mixture is stirred at 90° C. for 2 hours. Triethylamine (1.4 ml, 1.0 g, 0.010 mol) is metered in and the mixture is stirred at 90° C. for a further 3 hours. After cooling, the product is filtered off with suction and washed with 3×20 ml of toluene and dried. 21.0 g of 3-(4-chlorophenyl)-2,4(1H,3H)-quinazolinedione (yield: 77.0% of theory) of melting point 288° to 290° C. are obtained. According to thin-layer chromatography, the product is contaminated with the intermediate ethyl N-(4-chlorophenylcarbamoyl)anthranilate.

Example 6.2

Attempt at the Preparation of 3-(2,4-dichlorophenyl)-6-fluoro-2,4(1H,3H)-quinazolinedione in Xylene (Comparison Example Catalyst: Triethylamine)—Analogously to Example 5.1

A solution of 2,4-dichlorophenyl isocyanate (47.0 g, 0.25 mol) in xylene (130 ml) is metered at room temperature into a solution of ethyl 5-fluoroanthranilate (45.2 g, 0.25 mol) in xylene (210 ml). After addition is complete, the mixture is stirred at 90° C. for 2 hours. Triethylamine (3.5 ml, 2.55 g, 0.025 mol) is metered in. The mixture is stirred at 90° C. for a further 2 hours. After cooling, the product is filtered off with suction and washed with 3×30 ml of xylene and dried. 86.9 g of ethyl N-(2,4-dichlorophenylcarbamoyl)-5-fluoroanthranilate of melting point 219° to 223° C. (decomposition) are obtained. The cyclization product 3-(2,4-dichlorophenyl)- 6-fluoro-2,4(1H,3H)-quinazolinedione cannot be detected by thin-layer chromatography.

We claim:

1. A process for the preparation of quinazoline-2,4-diones of the formula (I)

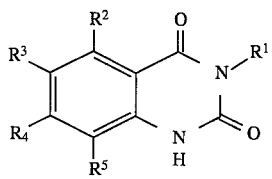

in which $R^1$ is aryl and $R^2$, $R^3$, $R^4$, and $R^5$ independently of one another are halogen, alkyl, alkoxy or hydrogen, which comprises reacting in a one pot process anthranilic acid esters of the formula (II)

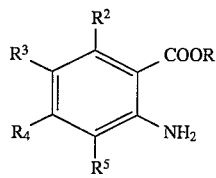

in which R is alkyl and $R^2$ to $R^5$ have the meaning indicated above, in an aprotic reaction medium with aryl isocyanates $R^1$—N=C=O to give N-arylcarbamoyl-anthranilic acid esters of the formula (III)

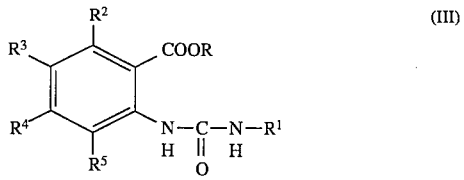

in which R and $R^1$ to $R^5$ have the meaning indicated above, and cyclizing these in the presence of a base selected from the group consisting of alkali metal alkoxide, alkaline earth metal alkoxide, alkali metal amide, alkaline earth metal amide alkali metal hydride, alkaline earth metal hydride and tetraalykylammonium hydroxide under formation of an alcohol ROH where R is as defined above and wherein the process is carried out in one and the same reaction medium.

2. The process as claimed in claim 1, wherein $R^1$ is phenyl which can be substituted by halogen, $(C_1–C_4)$-alkyl or $(C_1–C_4)$-alkoxy, R is $(C_1–C_3)$-alkyl and $R^2$ and $R^5$ independently of one another are hydrogen, $(C_1–C_3)$-alkyl, $(C_1–C_3)$-alkoxy, fluorine, chlorine or bromine.

3. The process as claimed in claim 1, wherein the aprotic reaction medium employed is an aromatic, cycloaliphatic or aliphatic hydrocarbon, heterocycle or ketone.

4. The process as claimed in claim 1, wherein the aprotic reaction medium employed is an aromatic hydrocarbon.

5. The process as claimed in claim 1, wherein the alkali metal or alkaline earth metal alkoxides, amides, hydrides or tetraalkylammonium hydroxides are employed in amounts from 1 to 95 mol %.

6. The process as claimed in claim 1, wherein in the cyclization step sodium methoxide is used in the form of its solution in methanol.

7. The process as claimed in claim 1, wherein the reaction of the aryl isocyanate with the anthranilic acid ester is carried out at temperatures from 20° to 150° C.

8. The process as claimed in claim 1, wherein the reaction temperature of the cyclization is chosen such that a resulting alcohol ROH distils off from the reaction medium.

9. The process as claimed in claim 2, wherein $R_2$ and $R_5$ independently of one another are hydrogen, fluorine, chlorine or methyl.

10. The process as claimed in claim 4, wherein the aromatic hydrocarbon is alkylbenzene.

11. The process as claimed in claim 4, wherein the aromatic hydrocarbon is xylene or its isomer mixture.

12. The process as claimed in claim 5, wherein the alkali metal or alkaline earth metal alkoxides, amides, hydrides or tetraalkylammonium hydroxides are employed in amounts from 1 to 20 mol % based on (III).

13. The process as claimed in claim 5, wherein the alkali metal or alkaline earth metal alkoxides, amides, hydrides or tetraalkylammonium hydroxides are employed in amounts from 5 to 10 mol % based on (III).

14. The process as claimed in claim 7, wherein the temperature is from 30° to 120° C.

* * * * *

UNITED STATES PATENT AND TRADEMARK OFFICE
CERTIFICATE OF CORRECTION

PATENT NUMBER: 5,539,114

DATED: July 23, 1996

INVENTOR(S): Robert Cosmo, Darmstadt; Wolfgang Tronich, Eppstein,

It is certified that errors appear in the above-identified patent and that said Letters Patent is hereby corrected as shown below:

In claim 5, at column 8, line 35 at the end of the line please insert --based on (III)--.

Signed and Sealed this

Twenty-fifth Day of March, 1997

Attest:

BRUCE LEHMAN

*Attesting Officer*  Commissioner of Patents and Trademarks